United States Patent [19]
Zeller et al.

[11] 4,454,331
[45] Jun. 12, 1984

[54] PROCESS FOR PREPARING TETRAFLUOROETHYLOXYALKYL SILANES

[75] Inventors: Norbert Zeller; Rudolf Riedle, both of Burghausen; Tassilo Lindner, Mehring-Oed, all of Fed. Rep. of Germany; Wolfgang Wagner, Tokyo, Japan

[73] Assignee: Wacker Chemie GmbH, Munich, Fed. Rep. of Germany

[21] Appl. No.: 401,785

[22] Filed: Jul. 26, 1982

[30] Foreign Application Priority Data

Sep. 25, 1981 [DE] Fed. Rep. of Germany ....... 3138236

[51] Int. Cl.³ .............................. C07F 7/08; C07F 7/18
[52] U.S. Cl. ...................................... 556/448; 556/479
[58] Field of Search ................................ 556/479, 448

[56] References Cited

U.S. PATENT DOCUMENTS 4,276,426  6/1981  Lindner et al. ...................... 564/479

OTHER PUBLICATIONS

"Proc. Acad. Sci. USSR," Chem. Sect., 124, p. 838, 1959.

*Primary Examiner*—Paul F. Shaver

[57] ABSTRACT

This invention relates to a process for preparing tetrafluoroethyloxyalkyl silanes by the addition of silanes containing Si-bonded hydrogen to tetrafluoroethylalkenylether in a tubular reactor in which the reaction mixture containing an excess of silanes is recycled at a rate of at least 10 meters per minute.

5 Claims, No Drawings

PROCESS FOR PREPARING TETRAFLUOROETHYLOXYALKYL SILANES

The present invention relates to tetrafluoroethyloxyalkyl silanes and particularly to a process for preparing tetrafluoroethyloxyalkyl silanes. More particularly this invention relates to a process for preparing tetrafluoroethyloxyalkyl silanes by the addition of silanes containing Si-bonded hydrogen to a tetrafluoroethyloxy compound having an aliphatic multiple bond.

BACKGROUND OF THE INVENTION

A process for preparing tetrafluoroethyloxypropyl methyldichlorosilane by reacting methyldichlorosilane with tetrafluoroethylallyl ether in the presence of a platinum-carbon catalyst in an autoclave at 11 bar (abs.) is described in Proc. Acad. Sci. USSR, Chem. Sect. 124,838, 1959. However, in this process a yield of only about 35 percent tetrafluoroethyloxypropyl methyldichlorosilane is obtained.

Also, U.S. Pat. No. 4,276,426 to Lindner et al, describes a process for preparing organosilicon compounds in a tubular reactor, by reacting silanes containing Si-bonded hydrogen with compounds having an aliphatic multiple bond, in which the reaction mixture is recycled at a rate of at least 10 meters per minute.

Therefore, it is an object of the present invention to provide a process for preparing tetrafluoroethyloxyalkyl silanes. Another object of this invention is to provide a process for preparing tetrafluoroethyloxyalkyl silanes in high yields. A further object of this invention is to provide a process for preparing tetrafluoroethyloxyalkyl silanes in which the fluorine exchange reaction is kept to a minimum.

SUMMARY OF THE INVENTION

The foregoing objects and others which will become apparent from the following description are accomplished in accordance with this invention, generally speaking, by providing a process for preparing tetrafluoroethyloxyalkyl silanes which comprises reacting in a liquid phase a silane having Si-bonded hydrogen with a tetrafluoroethyloxy compound having an aliphatic multiple bond in a tubular reactor, in which the reaction mixture is recycled at a rate of at least 10 meters per minute and the silane containing Si-bonded hydrogen is present in an amount in excess of the tetrafluoroethyloxy compound present in the reaction mixture.

DETAILED DESCRIPTION OF THE INVENTION

Silanes having Si-bonded hydrogen which are used in this invention may be represented by the following general formula

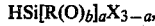

wherein R represents the same or different monovalent hydrocarbon radicals or substituted monovalent hydrocarbon radicals free of aliphatic multiple bonds, having from 1 to 18 carbon atoms, X represents the same or different halogen atoms, a is 0, 1, 2 or 3, and b is 0 or 1.

Examples of hydrocarbon radicals represented by R are alkyl radicals, such as the methyl, ethyl, n-propyl, isopropyl, n-butyl, sec-butyl, and the 2-ethylhexyl radical, as well as octadecyl radicals; cycloalkyl radicals such as the cyclohexyl radical and aryl radicals, such as the phenyl radical. Examples of substituted hydrocarbon radicals represented by R are especially halogenated hydrocarbon radicals, such as the 1-chloropropyl radical. Halogen atoms represented by X are chlorine, bromine, iodine and fluorine, with chlorine being the preferred atom.

Specific examples of silanes containing Si-bonded hydrogen which may be used in this invention are trichlorosilane, methyldichlorosilane, trimethylsilane, methylphenylchlorosilane, dimethylchlorosilane, and trimethoxysilane.

The tetrafluoroethyloxy compounds containing an aliphatic multiple bond which may be used in this invention may be represented by the following general formula

wherein Q represents an aliphatic radical having from 2 to 6 carbon atoms with an aliphatic multiple bond, preferably an olefinic double bond.

Examples of radicals represented by Q are the vinyl, the allyl, the crotyl, the methallyl, the n-pentenyl, the 2,4,4-trimethylpentenyl and the n-hexenyl radicals.

Specific examples of tetrafluoroethyloxy compounds which may be used in the process of this invention are tetrafluoroethyl-vinylether and tetrafluoroethyl-allylether.

The silanes containing Si-bonded hydrogen which are used in the process of this invention are preferably used in an excess of from 10 to 25 mole percent based on the amount of tetrafluoroethyloxy compound present in the reaction mixture.

These reactions are carried out in the presence of a catalyst which promotes the addition of Si-bonded hydrogen to an aliphatic multiple bond. Catalysts which are especially preferred are the so-called hydrosilation catalysts which may be used in the homogeneous phase. Suitable examples of such catalysts are compounds or complexes of platinum, rhodium, palladium, cobalt, nickel and iron. Examples of preferred catalysts are platinum compounds and complexes such as $H_2PtCl_6.6H_2O$, platinum-olefin complexes, platinum-alcohol or platinum-alcoholate complexes, platinum-ether complexes, platinum-aldehyde complexes, platinum-ketone complexes, such as the reaction products of $H_2PtCl_6.6H_2O$ and cyclohexanone, platinum-vinylsiloxane complexes, such as platinum-divinyltetramethyldisiloxane complexes, bis-(rpicolin)-platinum dichloride, trimethylenedipyridine-platinum-dichloride, reaction products of $PtCl_4$ with olefin and primary and/or secondary amines, as well as iron, nickel and cobalt carbonyls.

In addition to the catalysts described above, the reaction mixture may contain accelerators such as phenothiazine, diphenylamine, N,N-diphenyl-p-phenylenediamine or phenoxazine.

The amount of catalyst employed in the reaction mixture is preferably from about $10^{-3}$ to $10^{-7}$ mole for each gram atom of Si-bonded hydrogen present in the reaction mixture.

The process of this invention is carried out as a continuous process in a tubular reactor. The reactants, including the catalyst and the accelerator, if desired, may be introduced into the reaction mixture intermittently or continuously as a mixture or separately. However, it is preferred that the reactants and the catalyst be introduced into the reactor separately and not as a mixture.

The tubular reactor is frequently built so as to form a loop within which the reaction mixture can be recirculated. The distance between the location where the reactants, including the catalyst, enter the reactor and the point where the reaction mixture exits from the reactor, is generally between 5 and 20 meters and preferably about 10 meters. The inside diameter of the reactor is generally between about 5 and 20 mm.

It is preferred that the reaction temperatures range from about 80° to about 120° C.

The pressure in the reactor is controlled so as to prevent the formation of a gaseous phase within the reactor. Generally, the pressure ranges from about 3 to about 6 bar (abs.).

The reaction mixture is recycled at a rate of at least 10 meters per minute. Generally, the reaction mixture is recycled at a rate of between 30 and 40 meters per minute, although there is no upper limit for recycling the reaction mixture.

The time the reaction mixture remains in the reactor is preferably controlled so that at least 90 mole percent of the total amount of tetrafluoroethyloxy compound is reacted before the reaction mixture is removed from the reactor. Generally, the contact time is from about 5 to 12 minutes.

Compositions which may be prepared from the process of this invention are, for example
tetrafluoroethyloxypropyl-trichlorosilane,
tetrafluoroethyloxypropyl-methyldichlorosilane,
tetrafluoroethyloxypropyl-dimethylchlorosilane,
tetrafluoroethyloxyethyl-trichlorosilane,
tetrafluoroethyloxyethyl-methyldichlorosilane,
tetrafluoroethyloxyethyl-dimethylchlorosilane,
tetrafluoroethyloxypropyl-trimethoxysilane,
tetrafluoroethyloxypropyl-triacetoxysilane.

The alkoxy and acyloxy silanes which may be obtained in accordance with this invention can also be prepared by conventional means by reacting the tetrafluoroethyloxyalkylhalosilanes in a second reactor with the corresponding alcohols or acid anhydrides.

With the process of this invention it is now possible to prepare tetrafluoroethyloxyalkyl silanes in increased yields, without appreciable fluorine exchange reactions, which normally occur in preparing such silanes and which generally result in the formation of compositions having Si-bonded fluorine, along with the simultaneous destruction or substitution of the tetrafluoroethyl group.

Silanes prepared in accordance with this invention as well as polymer species which can be derived from such silanes are used to treat textile materials and paper products to impart hydrophobic and oleophobic properties thereto. Also, these silanes are used for treating organic or inorganic solids, as anti-foaming agents and as lubricants.

The following examples are given to further illustrate the invention and are not intended for purposes of limitation. All percentages are by weight unless otherwise specified.

EXAMPLE 1

Preparation of tetrafluoroethyloxypropyl-trichlorosilane.

The reactor consists of a U-shaped 10 meter long steel pipe having a helical configuration and an inside diameter of 9 mm. An aperture is provided at both ends of the U-shaped reactor for the entry and exit of the reaction mixture. A steel pipe having an inside diameter of 9 mm is connected to the pipe reactor very near the entry and exit apertures. This steel pipe is connected to a pump which recycles the reaction mixture at the rate of 35 meters per minute. The reaction temperature is 100° C. and the pressure is 5 bar, with the pressure being controlled by a pressure valve that is located near the outlet aperture of the reactor.

Each hour, 1.5 liters (11.3 moles) of tetrafluoroethylallylether, 1.3 liters (12.7 moles) trichlorosilane and 10 ml of a catalyst solution are added to the reactor. The catalyst solution is prepared by dissolving 19.4 g of tetrachlorodioctenediplatinum (II) in 1000 ml of chloroform.

About 3.1 kg per hour of the reaction mixture are continuously withdrawn which contains the following silicon compounds:
$HSiCl_3$—3.6 percent,
$SiCl_4$—0.7 percent,
$HCF_2CF_2OCH_2CH=CH_2$—0.6 percent,
$CH_3CH_2CH_2SiCl_3$—0.5 percent,
$HCF_2CF_2O(CH_2)_3SiCl_2F$—1.0 percent,
$HCF_2CF_2O(CH_2)_3SiCl_3$—91.6 percent.

The final product is a colorless liquid which has a boiling point of 74.5° C. at 15 mbar; a refractive index of $n_D{}^{25}=1.3970$; a density at 25° C. of 1.43 g/ml and a viscosity at 25° C. of 1.9 mm$^2$/s.

EXAMPLE 2

Preparation of tetrafluoroethyloxypropyl-methyldichlorosilane.

Each hour, 1.5 liters (11.3 moles) of tetrafluoroethylallylether, 1.4 liters (13.5 moles) of methyldichlorosilane and 15 ml of the catalyst solution described in Example 1, are added to the same reactor as used in Example 1. The reaction temperature is 100° C. and the operating pressure is 5 bar (abs.). About 3.3 kg per hour of the reaction mixture is removed having the following composition:
Propene—0.2 percent,
$HSi(CH_3)Cl_2$—4.8 percent,
$CH_3SiCl_3$—6.3 percent,
$HCF_2CF_2OCH_2CH=CH_2$—1.0 percent,
$CH_3CH_2CH_2Si(CH_3)Cl_2$—2.3 percent,
$HCF_2CF_2O(CH_2)_3Si(CH_3)F_2$—0.2 percent,
$HCF_2CF_2O(CH_2)_3Si(CH_3)ClF$—3.0 percent,
$HCF_2CF_2O(CH_2)_3Si(CH_3)Cl_2$—78.5 percent.

After vacuum distilling the final product, a colorless liquid having a boiling point of 80° C. at 10 mbar is obtained.

The colorless liquid has the following properties:
Refractive index: $n_D{}^{25}\mp 1,3930$.
Viscosity at 25° C.: 2.3 mm$^2$/s.
Density at 25° C.: 1.31 g/ml.

COMPARISON EXAMPLE 1

Preparation of tetrafluoroethyloxypropyl-methyldichlorosilane.

About 10 ml. of the catalyst solution prepared in accordance with Example 1 are placed in a reaction flask. Over a period of one hour and with agitation, a mixture consisting of 395.2 g (2.5 moles) of tetrafluoroethyl-allylether and 316.3 g (2.75 moles) of methyldichlorosilane is added dropwise. The reaction temperature is 100° C. About 704.7 g of a reaction mixture is obtained having the following composition:
Propene—0.5 percent, $HSi(CH_3)Cl_2$—10.1 percent,
$CH_3SiCl_3$—14.5 percent,
$HCF_2CF_2OCH_2CH=CH_2$—12.8 percent,
$CH_3CH_2CH_2Si(CH_3)Cl_2$—3.1 percent,
$HCF_2CF_2O(CH_2)_3Si(CH_3)F_2$—1.5 percent,
$HCF_2CF_2O(CH_2)_3Si(CH_3)ClF$—7.0 percent,
$HCF_2CF_2O(CH_2)_3Si(CH_3)Cl_2$—46.8 percent.

COMPARISON EXAMPLE 2

The process described in Example 2 above is repeated, except that equimolar quantities are employed, i.e., 11.3 moles tetrafluoroethyl-allylether and 1.18 liters (11.3 moles) of methyldichlorosilane.

About 3.0 kg per hour of a reaction mixture having the following composition is obtained.

Propene—0.9 percent,
$HSi(CH_3)Cl_2$—3.8 percent,
$CH_3SiCl_3$—4.9 percent,
$HCF_2CF_2OCH_2CH=CH_2$—9.8 percent,
$CH_3CH_2CH_2Si(CH_3)Cl_2$—5.7 percent,
$HCF_2CF_2O(CH_2)_3Si(CH_3)F_2$—1.4 percent,
$HCF_2CF_2O(CH_2)_3Si(CH_3)ClF$—6.2 percent,
$HCF_2CF_2O(CH_2)_3Si(CH_3)Cl_2$—62.5 percent.

When the results of Examples 1 and 2 are compared with Comparison Examples 1 and 2, they show that the silane must be used in excess, otherwise a substantial decrease in the yield is obtained.

What is claimed is:

1. A process for preparing tetrafluoroethyloxyalkyl silanes which comprises reacting a silane having an Si-bonded hydrogen with a tetrafluoroethyloxy compound having an aliphatic multiple bond in a liquid phase, in which the reaction mixture is recycled at a rate of at least 10 meters per minute and the silane having Si-bonded hydrogen is present in an amount of from 10 to 25 mole percent in excess of the tetrafluoroethyloxy compound present in the reaction mixture.

2. The process of claim 1, wherein the reaction is conducted in a tubular reactor.

3. The process of claim 1, wherein the reaction is conducted in the presence of a hydrosilation catalyst.

4. The process of claim 3, wherein the hydrosilation catalyst is present in an amount of from $10^{-3}$ to $10^{-7}$ mole for each gram atom of Si-bonded hydrogen.

5. The process of claim 1, wherein the reaction temperature ranges from about 80° to about 120° C.

* * * * *